United States Patent [19]
Hochman

[11] Patent Number: 5,849,990
[45] Date of Patent: Dec. 15, 1998

[54] ANIMAL MODEL FOR A NON-HODGKIN'S LYMPHOMA

[75] Inventor: Jacob Hochman, Jerusalem, Israel

[73] Assignee: Yissum Research Development Company of the Hebrew University of Jerusalem, Jerusalem, Israel

[21] Appl. No.: 358,911

[22] Filed: Dec. 19, 1994

[51] Int. Cl.$^6$ ............................. C12N 5/00; A61K 49/00
[52] U.S. Cl. ...................... 800/2; 800/DIG. 5; 435/354; 424/9.2
[58] Field of Search .................................. 800/2, DIG. 4, 800/5; 435/240.2; 424/9.1, 9.2

[56] References Cited

FOREIGN PATENT DOCUMENTS

EP 0 438 053 A1   7/1991   European Pat. Off. .
EP 0 517 199 A1   12/1992  European Pat. Off. .

OTHER PUBLICATIONS

"Intraocular Lymphoma—Clinical and Histopathologic Diagnosis", Scott M. Whitcup, MD, et al., Ophthalmology 1993; 100:1399–1406.
"Combined Modality Therapy for Primary CNS Lymphoma", Lisa M. DeAngelis, et al., Journal of Clinical Oncology, vol. 10, No. 4, Apr. 1994, pp. 635–643.
"Posterior Uveitis and Primary Cerebral Reticulum Cell Sarcoma", Richard E. Appen, MD, Arch Ophthalmol, vol. 93, Feb. 1975, pp. 123–124.
Combined Malignant Lymphoma of the Eye and CNA (Reticulum–Cell Saroma), Edward J. Rockwood, MD, et al., J. Neurosurg 61:369–374, 1984.
"Clinical Features, Laboratory Investigations, and Survival in Ocular Reticulum Cell Sarcoma", L. Neal Freeman, MD, et al,. Ophthalmology 94:1631–1639, 1987.
"The Role of Radiation Therapy in the Management of Ocular Reticulum Cell Sarcoma", Lewrence Margolis, MD, et al., American Cancer Society 45:688–692, 1980.
"Primary Lymphoma of the Central Nervous System", Chapter 353, Neoplastic Diseases of the Central Nervous System, p. 2019.
"Primary Central Nervous System Lymphoma", John W. Grant and Peter G. Isaacson, Brain Pathology 2:97–109, 1992.
"Primary Central Nervous System Involvement of the So–called 'Peripheral Tcell Lymphoma 'Report of a Case and Review of the Literature", Katsuyoshi Mineura, et al., Journal of Neuro–Oncology 16:235–242, 1993.
"Heterotransplanation of Human Lymphoid Neoplasms Using a Nude Mouse Intraocular Xenograft Model", Les White, et al., Cancer Research 50, 3078–3086, May 15, 1990.
"Mouse Myelomas and Lymphomas in Culture", K. Horibata, et al., Experimental Cell Research 60 (1970) pp. 61–77.
"Substrate–adhering Lymphoid Cells Show Impaired Tumorigenicity and Increased Immunogenicity", Jacob Hochman, et al., Nature, vol. 290, pp. 248–249, Mar. 19, 1981.
"Cell Adhesiveness is Related to Tumorigenicity in Malignant Lymphoid Cells", Jacob Hochman, et al., The Journal of Cell Biology, vol. 99, Oct. 1984, pp. 1282–1288.
Benke et al. (1988) Invasion Metastasis 8: 159–176.
Biondi et al. (1993) Leukemia 7: 281–289.
Ghetie et al. (1990) Int J Cancer 45: 481–485.
Kawata et al. (1994) Cancer Research 51: 2688–2694.

*Primary Examiner*—Bruce R. Campell
*Attorney, Agent, or Firm*—Wigman, Cohen, Leitner & Myers, P.C.

[57] ABSTRACT

A non-human animal model for CNS and eye-infiltrating lymphomas is produced by inoculating a rodent with the cells of a lymphoma causing cell line capable of infiltrating into the CNS or eye of the inoculated host.

6 Claims, 3 Drawing Sheets

ANIMAL MODEL FOR A NON-HODGKIN'S LYMPHOMA

FIELD OF THE INVENTION

The present invention concerns a non-human animal model for a human disease. The present invention further concerns cell lines useful in the production of such a model.

PRIOR ART

The following is a list of prior art references considered to be pertinent for the subsequent description:
1. Whitcup, S. M., de Smet, M. D., Rubin, B. I., Palestine, A. G., Martin, D. F., Burnier Jr., M., Chan, C. C. and Nussenblat, R. B., Intraocular lymphoma—clinical and histopathologic diagnosis, *Ophthalmology*, 100:1399–1406 (1993).
2. DeAngelis, L. M., Yahalom, J., Thaler, H. T. and Kher, U., Combined modality therapy for primary CNS lymphoma, *J. Clin, Oncol.*, 10:635–643 (1993).
3. Appen, R. E., Posterior uveitis and primary cerebral reticulum cell sarcoma, *Arch. Ophthalnzol.*, 93:123–124 (1975).
4. Rockwood, E. J., Zakov, Z. N., and Bay, J. W., Combined malignant lymphoma of the eye and CNS (reticulum-cell sarcoma), *J. Netirosurg.*, 61;369–374 (1984).
5 5. Freeman, L. N., Schachat, A. P., Knox, D. L. et al, Clinical features, laboratory investigations, and survival in ocular reticulum cell sarcoma, *Ophthalmology*, 94:1631–1639 (1987).
6. Marglis, L., Fraser, R., Lichter, A. and Char, D. H., The role of radiation therapy in the management of ocular reticulum cell sarcoma, *Cancer*, 45:688–692 (1980).
7. Wilson, S. D., Braunnvald, E., Isselbacher, K. J., McGrahill, Inc., Petersdorf, R. G., Martin, J. B., Fauci, A. S., and Root, R. K., 12th Edition, Harrison's Principles of Internal Medicine Eds., 2019, (1991).
8. Grant, J. W., and Isaacson, P. G., Primary central nerve system lymphoma, *Brain-Pathol.*, 2(2), 97–109 (1992).
9, Mineura, K., Sawataishi, J., Sasjima, T., Kowada, M., Sugawara, A. and Ebina, K., Primary central nervous system involvement of the so called 'peripheral T-cell lyniphoma'. Report of a case and review of the literature, *J. Neuro. Oncol.*, 16(3) 235–242) (1993).
10. White, L., Trickett, A., Morris, D. M., et al., Heterotransplantation of human lymphoid neoplasms using a nude mouse intraocular xenograft model, *Cancer Research*, 50:3078–3086 (1990).
11. Horibata, K., and Harris, A. W., Mouse myelomas and lymphomas in culture, *Exp. Cell Research*, 60:61–77 (1970).
12. Hochman, J., Katz, A., Levy, E. and Eshel, S., Substrate adhering lymphoid cells show impaired tumorigenicity and increased immuno-genicity, *Nature* (London) 290:248–249 (1981).
13. Hochman, J., Levy, E., Mador, N., Gottesman, M., Shearer, G. M. and Okon, E., Cell adhesiveness is related to tumorigenicity in malignant lymphoid cells, *J. Cell Biol.* 99:1282–1288 (1984).
14. Reisner, Y., (1991), European Patent Application, Publication Number 438053.
15. Reisner, Y., (1992), European Patent Application, Publication Number 517199.

The acknowledgement herein of any of the above references is to allow the reader to gain appreciation of the prior art. The acknowledgement should, however, not be construed as an indication that these references are in any way relevant to the issue of patentability of the invention as defined in the appended claims.

Acknowledgement of the above references will be made by indicating the number from the above list.

BACKGROUND OF THE INVENTION

Non-Hodgkin's lymphoma of the central nervous system (NHL-CNS) as well as systemic non-Hodgkin's lymphoma frequently result in lethal intraoccular lymphoma[1-4]. NHL-CNS arises within the brain, spinal cord, leptomeninges or the eye, but then is spread throughout the CNS with rare systemic spread outside the CNS. Against this, systemic non-Hodgkin's lymphoma almost always arises outside the CNS and often gives rise to spread of the tumor cells into the eye by invasion of the cells through the choroidal circulation followed often by development of clinically evident malignancies within the brain parenchyma or subarachnoid space.

In a study of 32 patients with histologically proven lymphoma of the eye, CNS involvement occurred in 18 patients (56%)[5]. In 82% of the latter patients, the eye symptoms preceded infiltration into the CNS. Most patients suffering from lymphoma of the eye die within 1 to 5 years of their diagnosis[6].

Recently, T and B lymphomas were detected in the brain of AIDS patients[7-9].

CNS and eye-infiltrating lymphomas are lethal diseases and development of therapies for the treatment of these diseases are highly desired. However, the pre-clinical study of such diseases which is required for the purpose of therapy development, is hindered by the fact that there are no good experimental models allowing the study of this kind of disease.

An animal model which has been used to date to study eye-infiltrating leukemias and lymphomas, involves injection of cells from childhood leukemias and lymphomas into the anterior chamber of the eye of nude mice[10]. However, the relevancy of this model is doubtful since the etiologically important step of infiltration cannot be reproduced in this animal model. Furthermore, since nude mice are immuno-deficient, any immuno-based selection forces acting in normal animals, are absent.

The T-25 cell line is a highly tumorigenic cellular subline derived from the S49 mouse T-cell lymphomna[11], and was derived therefrom by 25 passages in vivo[12]. Both the T-25 and the S49 cell line grow in culture as a cell suspension. By selection for adherence, a cell line termed "T-25-Adh" was obtained which has a low turmorigenicity and which adheres to a substrate. By UV-irradiation and selection for tumorigenicity, a cell line with a median tumorigenicity, termed "Rev-1" was obtained, which has the property of growing in culture as a suspension of cell clumps. By in vivo selection of this cell line, highly tumorigenic revertant cell lines were obtained[13] termed "Rev-1-T(a)" and "Rev-1-T(b)". The S49-cell lineage is depicted in FIG. 1.

The present invention is based on the surprising finding of a novel property of the T-25-Adh cell line, shared also by a cell line derived therefrom. This property allows the development of an animal model for non-Hodgkin's type lymphoma of the kind which infiltrates the CNS or the eye.

SUMMARY OF THE INVENTION

The present invention is directed, by one of its aspects, to an animal model of lymphoma of the kind which infiltrates the CNS or the eye (infiltration into the eye includes infiltration intra-occularly as well as infiltration into eyeassociated tissue, such as into the lacrimal glands). For the sake of simplicity, such infiltrating non-Hodgkin's lymphoma will be referred to collectively as "infiltrating NHL", it being understood that this term refers to both NHL which infiltrates either or both the CNS and the eye, including occular tissues which are not part of the CNS.

It is an object of the present invention to provide a non-human animal model for infiltrating NHL.

It is another object of the present invention to provide a method for screening of preventive or therapeutic agents of infiltrating NHL.

It is further an object of the present invention to provide a non-human animal model of gene expression within the eye or CNS.

It is a still further object of the present invention to provide cell lines useful for the construction of such a model.

Remaining objects of the invention will be realized from the description below.

The cells designated herein, above and below, as REV-2-T-6 cells have been deposited at the European Collection of Animal Cell Cultures (ECACC) under the Accession Number 94122103.

DETAILED DESCRIPTION OF THE INVENTION

In accordance with the present invention it has surprisingly been found that certain lymphoma cell lines and cell lines derived therefrom have the property such that upon their systemic inoculation, e.g. intraperitoneally (i.p.), into rodents, to cause lymphoma in the inoculated animals and also infiltrate into the CNS (e.g. the brain), into the eye (both CNS and non-CNS tissue of the eye) or into both the CNS and eye. Cells of cell lines of the kind used in accordance with the invention thus behave etiologically in a similar manner to that of an infiltrating NHL. Accordingly, rodents inoculated with such cells are useful, in accordance with the invention, as an animal model for infiltrating NHL. Such a model can be very advantageously used, for example, for screening of agents or treatment modalities for such that are useful in the treatment of infiltrating NHL or for such that are useful in the prevention of infiltration of lymphoma cells into the eye and/or CNS.

The cells of the invention can be "engineered" by various means known per se to the molecular biologist (the description of such means goes beyond the present writing), to express genes of interest. Rodents inoculated systemically with these engineered cells can then be used as animal models for such gene expression within the eye or brain.

The present invention provides by one of its aspects, a non-human animal model for infiltrating NHL, comprising a rodent host being inoculated systemically with cells of a tumorigenic cell line, which is either a lymphoma cell line or a cell line derived from a lymphoma cell line capable of causing lymphoma in the inoculated host and of infiltrating into the eye or CNS.

Systemic innoculation used above and below denotes an inoculation of cells which is not directly inoculated into a target organ, such as intraperitoncally, (i.p.) intravenously, subcutaneously or intramuscularly.

Also provided, in accordance with another aspect of the invention, are cells of a novel tumorigenic cell line, of a kind capable of causing lymphoma in an inoculated rodent host and infiltrating into the eye or CNS. Such cells are useful for the production of the above animal model.

The cell line may in principle be of any animal origin, e.g. human or rodent. The rodent host may be an immunocompetent host which may be selected from a range of rodents customarily used in laboratories, e.g., BALB/c mice; alternatively, the rodent host may be an immunodeficient host, e.g., a genetically immunodeficient rodent such as the SCID, Nude, Beige and BNX mice, or a rodent which was immunocompromised by irradiation or appropriate chemical treatment and whose immune system was then reconstituted by a bone marrow of SCID mice, such as that described in European Patent Applications Nos. 438053 and 517199[14, 15].

When an immunocompetent rodent is used as a host, it is usually preferred to use a lymphoma cell line from the same species, particularly such a cell line which is histocompatible to the host. Where an immune deficient host is used, the lymphoma cell line may be syngeneic, allogeneic or xenogencic.

The rodent is typically a mouse and the lymphoma cell line is typically a murine lymphoma cell line.

Some lymphoma cell lines, e.g., the T-25 cell line, are very violent and bring to death within a very short period of time insufficient to allow infiltration of the lymphoma cells into the brain or eye and the development of tumor foci there, even where the cell line has infiltrating properties. Thus, the cell lines to be used in accordance with the invention should have a median tumorigenicity, i.e., the median survival time of inoculated host is sufficient to allow infiltration of the lymphoma cells into the CNS or eye and the development of tumor foci there.

Lymphoma cells which grow in culture as a cell suspension usually bring to tumor-associated death following inoculation within a relatively short period of time, and are usually unsuitable for use in the production of an animal model in accordance with the invention. Cell lines derived from lymphoma cell lines which have the property of adhering either to a substrate or to one another, the latter type of which typically grows in culture as suspension of clumps of cells, bring to death of an inoculated animal within a longer period of time. Where the cells have CNS and eye infiltrating properties, such period of time would suffice for infiltration and appearance of tumor foci within the host animals' CNS or eye.

Two examples of such cells which were used effectively for the development of an infiltrating NHL model in accordance with the invention, were the T-25-Adh, which is a cellular subline of the T-25 cell line, which was known to date (see description of prior art under "Background on the Invention"), but which was not known to possess this property prior to the present invention; and another cell line, newly isolated in accordance with the present invention, designated herein as "Rev-2-T-6" and which was derived from the T-25-Adh cell line, as will be described further below.

An example of a suitable lymphoma cell line is such wherein after inoculation into a rodent of a quantity of such cells which brings to the occurrence of tumors in the inoculated rodent, e.g. $10^6$–$10^8$ cells, the median survival time of the tumor-bearing rodents is at least about 30 days, typically 50–80 days.

A unique finding in accordance with the invention is that the model is best achieved when using newborn rodents, i.e., 5–10 days postnatal. Accordingly, use of newborn rodents as the inoculated host is preferred in accordance with the invention.

The animal model of the invention is useful for the screening of agents or treatment modalities, (e.g., anti-cancer drugs, antibodies, combination of drugs, or administration regimens), having efficacy in the therapy of infiltrating NHL. For such screening, host rodents are inoculated with cells of the above type and, following a time interval sufficient to allow development of tumor foci within the brain and eye of the inoculated host, the host is then administered with the tested agent or treatment modality and the therapeutic effect of such agent or treatment can then be evaluated, for example by determining the animals' median survival time or by means of histopathology of the brain or eye.

The model can also be used for screening of therapeutic agents or treatment modalities for such having efficacy in the prevention of cell infiltration into the CNS and eye. For such screening, rodents are inoculated with a tumor-causing quantity of cells, similarly as above, and within a time interval prior to the beginning of infiltration of cells into the CNS or eye, e.g. at the same time or shortly after the inoculation of the cells, the host rodent is administered with the tested agent or treatment modality. The effect of the agent in preventing infiltration of the cells into the CNS or eye can then be determined, e.g. by histopathology.

The cells to be inoculated may be "engineered", by various molecular biology means known to the artisan, to express various genes of interest, e.g., genes conferring multi-drug resistance (MDR). Thus, following inoculation of such engineered cells into the rodents, the animals, with such cells infiltrated into their CNS or eye, can be used as a model for the respective gene expression within the CNS or eye. For example, where cells expressing the MDR gene are used, the inoculated animals may be used as a model for studying therapies effective in counter-acting the MDR activity within the brain and which thus render the cells sensitive to anti-cancer drugs.

The invention will now be illustrated by some non-limiting, specific embodiments described in the following examples.

Figure 1:
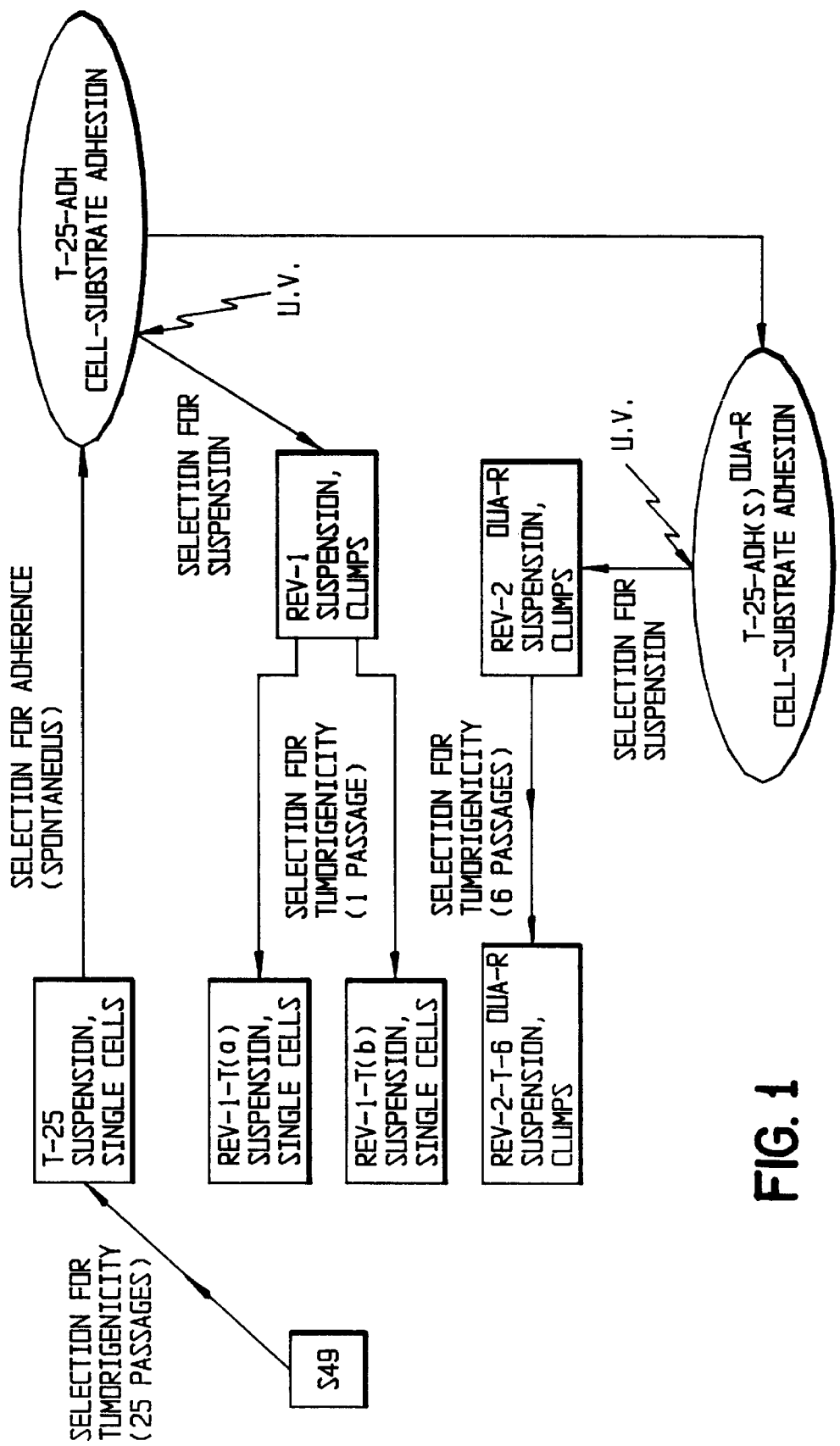
FIG. 1 shows the lineage of the S49 cell line. The horizontal position of the cell lines within the figure represents their tumorigenicity which decreases towards the right-hand side of the Figure. High tumorigenicity means that inoculation of these cells into mice give rise to tumors in a large proportion of the inoculated mice with a short median survival rate of the tumor-bearing mice; low tumorigenicity means low incidence of occurrence of tumors with a high survival rate of the tumor-bearing mice. For example, inoculation of the $10^6$ cells of the T-25 cell line brings to development of tumors in 100% of the inoculated mice and the median survival time of the tumor bearing mice is about 15 days. Inoculation of $3 \times 10^6$ cells of the Rev-2-T-6 cell line results in the development of tumors in about 90% of the inoculated mice and the median survival time of the tumor bearing mice is in the range of about 20–80 days. The Rev-2-T-6 cell lines thus has lower tumorigenicity than either T-25 or Rev-1-T(a) cells, as reflected by its horizontal position in the figure.

Of the cell lines shown in FIG. 1, the S49, T-25, T-25-Adh, Rev-1 and Rev-1-T(a) and Rev-1-T(b), were hitherto known; the cell lines derived from the T-25-Adh cell line, namely the cell line T-25-Adh(s) which is a result of selection for Ouabain resistance ("OUA-R"), and cell lines derived from the T-25-Adh(s), the Rev-2 and Rev-2-T-6 cell lines, are novel cell lines. Although cell line T-25-Adh was known, the property of this cell line, i.e., its capability to infiltrate the CNS or eye, is a novel property discovered in accordance with the invention.

Figure 2:
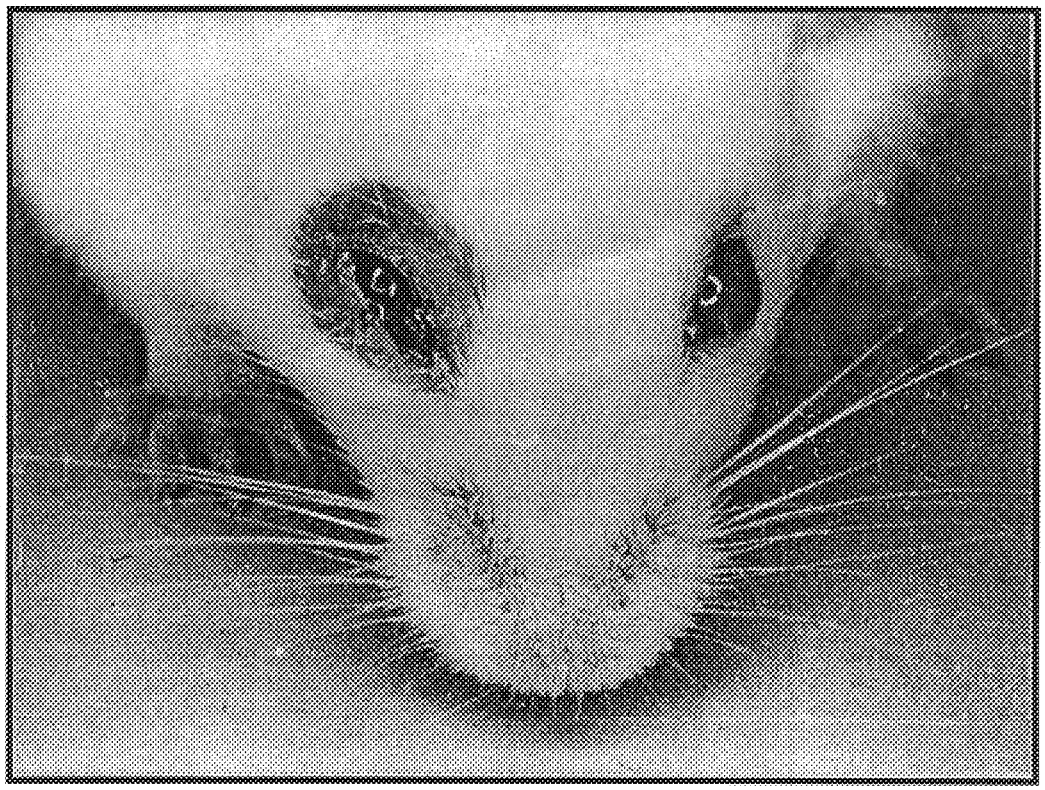

FIG. 2 is a photograph of a BALB/c mouse inoculated with Rev-2-T-6 cells showing the tumorous mass in the right orbit infiltrating the skin around the eye.

Figure 3A:
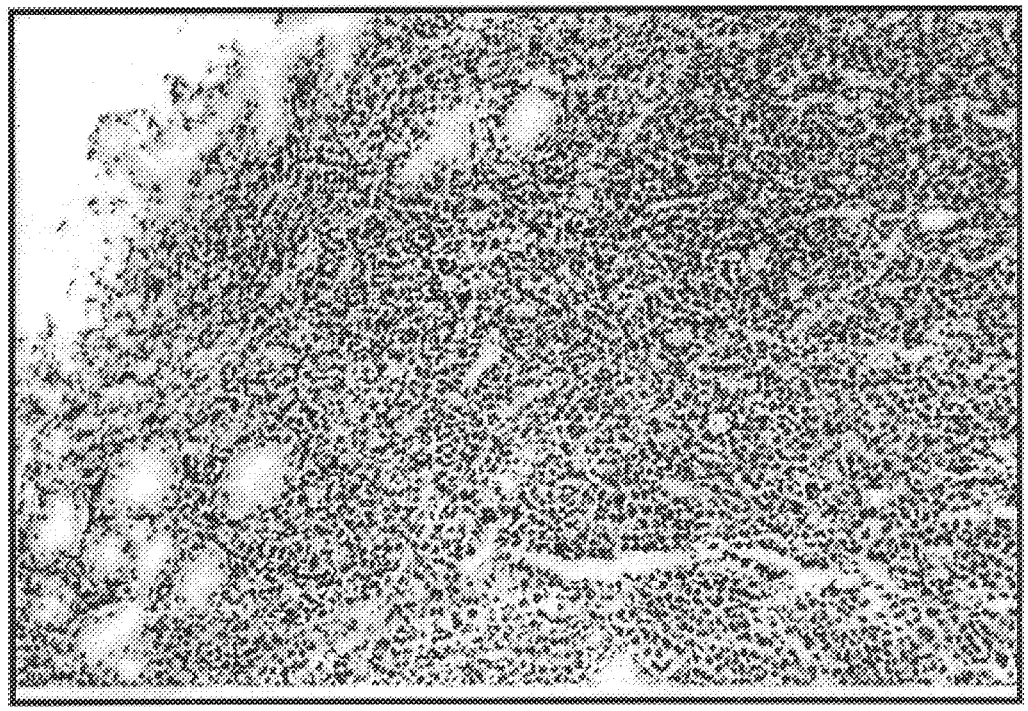
Figure 3B:
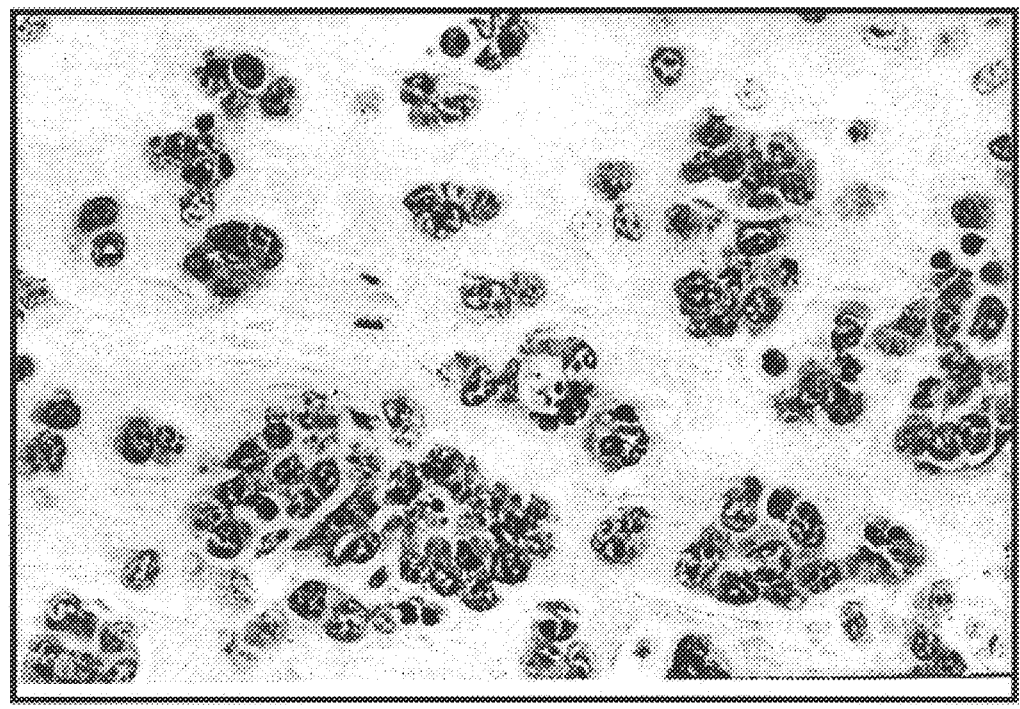

FIGS. 3A–3B shows histological sections of the eye and brain of the mouse shown in FIG. 2. In this FIG., FIG. 3A is a photograph of a histological section from the orbit of the right eye showing infiltration of a malignant lymphoma into the lacrimal gland. The normal structure of the gland is destroyed with remnants of normal lacrimal glands seen in the left corner of the picture. FIG. 3B is a photograph of a section of the brain of the inoculated mouse revealing clusters of malignant lymphoma cells in the brain's parenchyma.

EXAMPLE 1

Generation of Tumorigenic Revertants from T-25-Adh Cells

Cell-substrate adherent T-25-Adh cells were propagated in Dulbecco's Modified Eagle's Medium (DMEM) (Gibco) supplemented with 10% heat inactivated horse serum (Biological Industries—Beth Haemek, Israel), Penicillin (50 u/mil) and Streptomycin (50 mg/ml), Cells were maintained at 37° C. in a humidified atmosphere containing 5% $CO_2$. The adherent cells were selected in vitro for Ouabain resistance (OUA-R) by known methods. The resulting T-25-Adh cells were subjected in vitro to 30–50 mJoule of UV radiation. Culture plates in which 10–20% of the cells survived following the irradiation were further propagated and selected for cells growing in suspension. The resulting revertant cells, termed "Rev-2" cells were found to grow in suspension in the form of cellular clumps. Rev-2 cells were then injected into BALB/c mice at a dosage of $10^7$ cells/mouse and, after six passages in mice, high tumorigenic revertants, termed "Rev-2-T-6" cells were obtained. These cells were found to grow in vitro in the form of a suspension of large clumps.

The S49 cell lineage is shown in FIG. 1, in which both the prior art cell lines as well as the cell lines obtained in accordance with the invention are depicted.

EXAMPLE 2

Tumorigenicity of Rev-2-T-6 Cells in BALB/c Mice

Rev-2-T-6 cells were inoculated intraperitoneally (IP) into the following two groups of syngeneic BALB/c male mice at a concentration of $2 \times 10^7$ cell/mouse: Group 1: Newborn mice at the age of 5–8 postnatal days. Group 2: 8–10 weeks old immunocompetent mature mice. The results are shown in the following Tables 1 and 2.

TABLE 1

Newborn Mice (5–8 days postnatal)

| Cell line | Dosage - No. of cells/mouse | % Tumori- genicity*1 | % Infiltration into eye*2 | % Infiltration into CNS*3 | Median Survial time of tumor bearing mice in days |
|---|---|---|---|---|---|
| T-25 | $10^6$ | 100% | 0 | 0 | 12 |
| T-25-Adh | $2 \times 10^7$ | 31% | 6% | 20% | 30–140 |
| Rev-2-T-6 | $3 \times 10^6$ | 86% | 25% | 14% | 20–60 |

*1% Tumorigenicity = No. of mice devloping tumors/inoculated mice × 100
*2% Infiltration into eye = No. of mice with histopathological findings of malignant lymphoma cells in the eye/inoculated mice × 100
*3% Infiltration into eye = No. of mice with histopathological findings of malignant lymphoma cells in the CNS/inoculated mice × 100

TABLE 2

Mature mice (8–10 weeks)

| Cell line | Dosage - No. of cells/mouse | % Tumori- genicity*1 | % Infiltration into eye*2 | % Infiltration into CNS*3 | Median Survial time of tumor bearing mice in days |
|---|---|---|---|---|---|
| T-25 | $10^6$ | 100% | 0 | 0 | 17 |
| T-25-Adh | $2 \times 10^8$ | 0 | 0 | 0 | Not relevant |
| Rev-2-T-6 | $3 \times 10^6$ | 90% | 0 | 0 | 80 |

*1% Tumorigenicity = No. of mice devloping tumors/inoculated mice × 100
*2% Infiltration into eye = No. of mice with histopathological findings of malignant lymphoma cells in the eye/inoculated mice × 100
*3% Infiltration into eye = No. of mice with histopathological findings of malignant lymphoma cells in the CNS/inoculated mice × 100

As seen in the above Tables, injection of the Rev-2-T-6 cells into both newborn and mature mice resulted in progressive tumors in 90% of the mice. Eye and CNS involvement was not detected in any of the inoculated mature mice. Against this, 25% of the inoculated newborn mice showed infiltration of lymphoma cells into the eye and 14% of them showed lymphoma cells in the CNS. Injection of T-25-Adh cells caused tumors only in about 30% of the inoculated mice, however, 6% of the mice showed infiltration of lymphoma cells into the eye and 20% of them showed infiltration of lymphoma cells into the CNS. Injection of even high dosages of the T-25-Adh cells into mature mice did not cause tumors in any of the mice. Against this, injection of cells from the T-25 cell line into both newborn and mature mice resulted in tumors in 100% of the mice but none of the mice showed infiltration of lymphoma cells either into the eye or the CNS. As seen, the median survival time of mice inoculated with the T-25-Adh or Rev-2-T-6 cells was long (about 80 and 60 days, respectively) as compared to the short median survival time of mice injected with the T-25 cells (about 15 days).

FIG. 2 is a photograph showing one of those animals inoculated with the Rev -2-T-6 cells and which showed infiltration of the cells into the right eye orbit, evidenced by a round dark skin mass. Histological analysis showed that there was an infiltration of malignant lymphoma cells into the right lacrimal gland (FIG. 3a) and that tumor foci were observed in the brain parenchyma (FIG. 3b).

I claims:

1. A non-human animal model for infiltrating non-Hodgkins lymphoma comprising a BALB/c mouse inoculated with cells of the tumorigenic cell line REV-2-T-6 deposited with the European Collection of Animal Cell Cultures (ECACC) having Accession No. 94122103, wherein said tumorigenic cells are capable of infiltrating into the eye or central nervous system of said mouse.

2. The animal model according to claim 1, wherein the median survival time of the inoculated mouse following inoculation is at least about 30 days.

3. A method for evaluating an agent for treating lymphoma, comprising:
   (a) providing a BALB/c mouse which is inoculated with cells of the REV-2-T-6 cell line, deposited with the European Collection of Animal Cell Cultures (ECACC) having Accession No. 94122103;
   (b) administering said agent to said inoculated BALB/c mouse; and
   (c) evaluating the anti-tumor activity of said agent.

4. The method according to claim 3, wherein the agent is administered to the mouse for a time sufficient for the development of tumor foci within the inoculated mouse's eye or CNS.

5. A method for evaluating the potential of an agent, or a combination of agents, for the prevention of infiltration of lymphoma cells into the eye and/or central nervous system comprising the step of:
   (a) providing a BALB/c mouse inoculated with REV-2-T-6 cells deposited with the European Collection of Animal Cell Cultures (ECACC) having Accession No. 94122103;
   (b) administering said agent or said combination of agents to said inoculated mouse, the administration being within a time period after inoculation of said cells and before the said cells infiltrate the brain; and
   (c) evaluating the effectiveness of said agent or said combination of agents in the prevention of the development of tumor foci in the mouse's eye or eye and CNS.

6. Cells of the cell line designated herein, as REV-2-T-6 deposited at the ECACC under the Accession No 94122103.

* * * * *